United States Patent [19]

Schneider et al.

[11] 4,117,163

[45] Sep. 26, 1978

[54] BROAD SPECTRUM FUNGICIDAL DIACYLIMIDE COMPOSITIONS

[75] Inventors: Louis Schneider, Elizabeth; David E. Graham, Westfield, both of N.J.

[73] Assignee: GAF Corporation, New York, N.Y.

[21] Appl. No.: 852,459

[22] Filed: Nov. 17, 1977

[51] Int. Cl.$^2$ .............................................. A01N 9/20
[52] U.S. Cl. .................................................... 424/320
[58] Field of Search ........................................ 424/320

[56] References Cited

FOREIGN PATENT DOCUMENTS 42-1,313  11/1967  Japan ........................................ 71/118

OTHER PUBLICATIONS

Durrell et al; J. Org. Chem. vol. 28; 1963 pp. 831-833.

*Primary Examiner*—Allen J. Robinson
*Attorney, Agent, or Firm*—Walter C. Kehm; Walter Katz

[57] ABSTRACT

The invention provides broad spectrum fungicidal diacylimide compositions which include compounds having the formula:

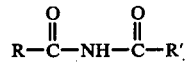

where R and R' are selected from alkyl, alkenyl, haloalkyl and haloalkenyl having from 1-5 carbon atoms, being the same or different groups.

The compositions of this invention show excellent agricultural fungicidal activity, particularly against bean rust, rice spot, tomato blight and other agricultural pathogens.

The diacylimide compounds generally are prepared by reacting a suitable amide with an acyl halide. The acyl halide precursor may be prepared, if necessary, from the corresponding acid by reaction with a suitable halogenating agent, such as thionyl chloride. Similarly, a given amide may be readily prepared, for example, from the corresponding acyl halide by reaction with ammonia.

2 Claims, No Drawings

BROAD SPECTRUM FUNGICIDAL DIACYLIMIDE COMPOSITIONS

BACKGROUND OF THE DISCLOSURE

1. Field of the Invention

This invention relates to novel fungicidal diacylimide compositions which are useful as agricultural fungicides.

2. Description of the Prior Art

Many compositions are known in the literature which are active as fungicides; however, the compounds of this invention show broad spectrum fungicidal activity, particularly against many agricultural pathogens.

SUMMARY OF THE INVENTION

The invention provides broad spectrum fungicidal diacylimide compositions which include compounds having the formula:

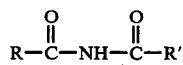

where R and R' are selected from alkyl, alkenyl, haloalkyl and haloalkenyl having from 1-5 carbon atoms, being the same or different groups.

The compositions of this invention show excellent agricultural fungicidal activity, particularly against bean rust, rice spot, tomato blight and other agricultural pathogens.

DETAILED DESCRIPTION OF THE INVENTION

The fungicidal compounds of the invention are prepared from a suitable amide I which is condensed with an acyl halide II to provide the desired diacylimide compound III, as follows:

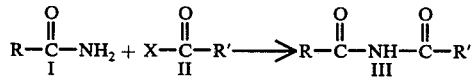

where R and R' are previously defined, and X is a halogen.

Both the acyl halide and amide starting materials usually are commercially available; however, if necessary, the acyl halide may be readily prepared from the corresponding acid by reaction with a suitable acyl halide, such as thionyl chloride. The amide may be readily prepared, for example, from the corresponding acyl halide by reaction with ammonia.

A. Agricultural Fungicidal Activity

As agricultural fungicides, the compositions of this invention usually are applied to the soil at the rate of about 1 to 25 lbs. per acre or as a foliar spray at concentrations of about 31 to 250 ppm. They show particularly effective foliar fungicidal activity against such fungi as bean rust, rice spot and tomato early blight.

The materials of the present invention may be applied to the soil or sprayed on the fungus susceptable plants on site at a rate of about 1 or less to about 25 pounds per acre depending on various circumstances of the susceptibility of the plant to the fungicide, the weather, the stage of growth and various other factors. The material may be applied as a dust or spray. As a dust, it is more practical to extend it with diluents such as bentonite, chalk, clay, diatomaceous earth, fullers earth, mica, ground slate or any of the other usual carriers for agricultural chemicals. As a spray, it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the weed.

B. Agricultural Foliage Fungicidal Tests

1. Tomato Early Blight

The compounds of the invention were tested on tomato early blight as follows: Young tomato seedlings 4 to 5 weeks of age were atomized while rotating on a turntable with a suspension of the test material diluted to 250 ppm. After the deposit dried, the plants were atomized with a spore suspension and incubated in a humidity cabinet at 70° to 75° F. for 24 hours. Then they are held in a greenhouse until lesions appear (usually 2 to 3 days.) The severity of infection is rated on a scale of 0 (no reduction) to 10 (complete elimination of infection) versus the standard Maneb, manganese ethyl bisdithiocarbamate.

2. Bean Rust

The compounds were tested on bean rust as follows: Pinto beans grown in 2.5 inch pots for 9 to 12 days is sprayed while plants are rotating on a turntable with 100 ml. of a formulation at 250 ppm. After the spray deposit dries, plants are placed in a moist chamber at 70° F. for 24 hours. After 7 to 9 days the severity of pustule formation is rated as above and compared with the commercial standard Plantvax, 2,3-dihydro-5-carbanilido-6-methyl-1,4-oxathiin-4,4-dioxide.

3. Rice Leaf Spot

Foliage protection and systemic eradication of the fungus is made on fully expanded young leaves of rice, cultivar Star Bonnet. In the primary test young plants about 2 weeks old growing in a 2½" pot are sprayed while rotating on a turntable with a suspension containing 250 ppm of a material. The soil is immediately drenched with 21 ml of a 520 ppm suspension (equivalent to a rate of 25 lb/acre). After the spray deposit dries, the plants are atomized with conidial suspension and placed in a moist chamber at 75° F. for 24 hours to facilitate infection. After discrete lesions appear in the unprotected controls (2 days later), the infection is rated on a scale from 0 (no inhibition) to 10 (complete inhibition of infection). As a standard fungicide, Daconil at 250 and 50 ppm or Maneb at 200 and 50 ppm are used as foliage protectants. There is no commercially acceptable systemic protectant.

The results of the above tests are given in Table I below.

Table I $$\underset{\text{Foliar Fungicidal Data}}{\overset{\overset{O}{\|}\qquad\overset{O}{\|}}{R-C-NH-C-R'}}$$

| Compound No. (B-T) | GAF No. | R | R' | Bean Rust | Rice Spot | Tomato Early Blight |
|---|---|---|---|---|---|---|
| 409 | 7201 | $ClCH_2CH_2-$ | $-CCl=CHCl$ | 9 | — | — |
| 519 | 7282 | $ClCH_2CH_2-$ | $-CH_2Br$ | 9 | 8 | — |
| 130 | 6790 | $CH_2=C(CH_3)-$ | $-C(CH_3)=CH_2$ | — | — | 8 |
| 410 | 7202 | $CH_2CH_2-$ | $-CH_2Cl$ | 10 | — | — |
| 4a | 6672 | $CH_2=CH-$ | $-CH=CH_2$ | 10 | 9 | — |
| 367 | 7181 | $ClCH_2-$ | $-CCl=CHCl$ | 9 | — | — |
| Control | | Plantvax | (Bean Rust) | 10 | — | — |
| Control | | Daconil | (Rice Spot) | — | 10 | — |
| Control | | Maneb | (Tomato Early Blight) | — | — | 10 |

The invention will be illustrated more, particularly by the following non-limiting specific examples by which the compounds in Table I are prepared.

EXAMPLE 1

N-CHLOROACETYL-N-2,3-DICHLOROACRYLOYLIMIDE

A. 2,3-Dichloroacryloylchloride 2,3-Dichloroacrylic acid (211.5g, 1.5 moles), thionyl chloride (357.0g, 3.0 moles), dimethylformamide (7cc) and benzene (300cc) were charged into a 1-liter, 4-neck flask and heated at reflux for 8 hrs. The benzene and excess thionyl chloride were removed atmospherically and 174.5g (73% yield) of product was distilled at 65°–67° C./23 mm.

B. 2,3-Dichloroacrylamide 2,3-Dichloroacryloylchloride (174.5g, 1.1 moles) was added to a 3-liter beaker precharged with aqueous ammonia (266cc, 4.4 moles) and ice (500cc). The mixture was stirred for ½ hr. at 0°–5° C., filtered and washed with cold water yielding 135g of amide (88%), m.p. 135°–136° C.

Anal: Calc'd for $C_3H_3Cl_2NO$: Cl, 50.71; N, 10.0. Found: Cl, 50.07; N, 9.69.

C. N-Chloroacetyl-N-2,3-Dichloroacryloylimide

Toluene (150cc), 2,3-dichloroacrylamide (52.0g, 0.37 mole) were charged into a 500 cc, 4-neck flask. Then chloroacetyl chloride (42.0g, 0.37 mole) was added and the reaction mixture was heated at reflux for 22 hrs. The mixture was cooled to 25° C. and the product filtered, washed with cold toluene and vacuum dried yielding 51g (63.8%) m.p. 99°–100° C.

Anal: Calc'd for $C_5H_4Cl_3NO_2$: Cl, 49.14; N, 6.47. Found: Cl, 49.16; N, 6.20.

EXAMPLE 2

N-Chloroacetyl-N-Propionylimide

Toluene (100cc), propionamide (7.3g, 0.1 mole) and chloroacetyl chloride (11.3g, 0.1 mole) were reacted and worked-up in a similar fashion as described in Example 1 to yield 5.5g (37.2%) of product m.p. 169°–170° C.

Anal: Calc'd for $C_5H_8ClNO_2$: Cl, 23.7; N, 9.36. Found: Cl, 23.6; N, 9.52.

EXAMPLE 3

N-Bromoacetyl-N-3-Chloropropionylimide

Toluene (100cc), 3-chloropropionamide (10.7g, 0.1 mole) and bromoacetyl chloride (20.2g, 0.1 mole) were reacted and worked-up in a similar fashion as described in Example 1 to yield 15.5g (71.6%) of product m.p. 133°–134° C.

Anal: Calc'd for $C_4H_7BrClNO_2$ Total halogen (Br, Cl) 50.5; N, 6.13. Found: Total Halogen (Br, Cl) 50.2; N, 6.25.

EXAMPLE 4

N-Acryloyl-N-Chloroacetylimide

Methylene chloride (150cc), chloroacetyl chloride (62.1g, 0.55 mole) and acrylamide (35.5g, 0.5 mole) were stirred at 25°–30° C. for 25 hrs. The product was filtered, washed with cold methylene chloride and dried to yield 17.0g (23.1%) of product, m.p. 175°–176° C.

Anal: Calc'd for $C_5H_6ClNO_2$: Cl, 24.0; N, 9.49. Found: Cl, 24.8; N, 9.26.

EXAMPLE 5

Bis-N,N-Methacryloylimide

Toluene (100 cc), methacrylamide (86g, 0.1 mole) and methacryloylchloride (10.5g, 0.1 mole) were reacted and worked in a similar fashion as described in Example 1 to yield 3.2 g (20.6%).

Anal: Calc'd for $C_8H_{11}NO_2$: N, 8.99. Found: N, 8.85.

In those diacylimides listed in Table I which contain an unsubstituted alkenyl group it is preferable to obtain these compounds by dehydrohalogenation of the corresponding haloalkenyl group, as for example, by refluxing with triethyl amine. A typical preparation according to this procedure is described in the following example.

EXAMPLE 6

N-Bromoacetyl-N-2,3-Dichloroacryloylimide

Toluene (100 cc), 2,3-dichloroacrylamide (14.0g, 0.1 mole), and bromoacetyl chloride (20.2g, 0.1 Mole) were reacted and worked-up in a similar fashion as described in Example 1 to yield 15.5g (59.4%) of product, m.p. 121°–122° C.

Anal: Calc'd for $C_5H_4BrCl_2NO_2$ Total Halogen (Br, Cl) 57.9; N, 6.14. Found: Total Halogen (Br, Cl) 58.8; N, 5.78.

What is claimed is:

1. A method of controlling fungi which comprises applying thereto a fungicidally effective amount of a diacylimide compound having the formula:

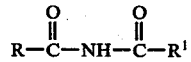

wherein R and $R^1$ being the same or different are selected from the group consisting of alkyl, alkenyl, haloalkyl and haloalkenyl groups having from 1–5 carbon atoms.

2. The method of claim 1, wherein R and $R^1$ are both haloalkenyl groups.

* * * * *